United States Patent
Dube et al.

(10) Patent No.: US 12,194,028 B2
(45) Date of Patent: Jan. 14, 2025

(54) STABLE PHARMACEUTICAL COMPOSITIONS OF APIXABAN

(71) Applicant: Slayback Pharma LLC, Princeton, NJ (US)

(72) Inventors: Sushant Omprakash Dube, Navi Mumbai (IN); Girish G. Kore, Solapur (IN); Naga Venkata Durga Prasad Ketha, Hyderabad (IN); Sumitra Ashokkumar Pillai, Hyderabad (IN); Praveen Kumar Subbappa, Princeton, NJ (US)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

(21) Appl. No.: 18/117,808

(22) Filed: Mar. 6, 2023

(65) Prior Publication Data

US 2023/0285368 A1    Sep. 14, 2023

(30) Foreign Application Priority Data

Mar. 9, 2022 (IN) .............................. 202241012898

(51) Int. Cl.
| | |
|---|---|
| *A61K 31/437* | (2006.01) |
| *A61K 47/10* | (2017.01) |
| *A61K 47/20* | (2006.01) |
| *A61K 47/26* | (2006.01) |
| *A61K 47/32* | (2006.01) |

(52) U.S. Cl.
CPC ............ *A61K 31/437* (2013.01); *A61K 47/10* (2013.01); *A61K 47/20* (2013.01); *A61K 47/26* (2013.01); *A61K 47/32* (2013.01)

(58) Field of Classification Search
CPC ...... A61K 31/437; A61K 47/10; A61K 47/20; A61K 47/26; A61K 47/32
See application file for complete search history.

(56) References Cited

U.S. PATENT DOCUMENTS

| | | |
|---|---|---|
| 9,452,134 B2 | 9/2016 | Badawy et al. |
| 10,016,362 B2 | 7/2018 | Badawy et al. |
| 2015/0224053 A1* | 8/2015 | Badawy ................. A61K 47/10 514/303 |

FOREIGN PATENT DOCUMENTS

CN     110615788 B   *  7/2021  .......... C07D 471/04

* cited by examiner

*Primary Examiner* — Jared Barsky
(74) *Attorney, Agent, or Firm* — Birch, Stewart, Kolasch & Birch, LLP (57) ABSTRACT

Liquid pharmaceutical compositions of apixaban or pharmaceutically acceptable salts thereof are described. More specifically, stable oral liquid pharmaceutical compositions of apixaban for oral administration are provided, wherein the composition is stable for extended periods of time. More specifically, stable liquid pharmaceutical compositions of apixaban at concentrations of 0.4 mg/mL or more are provided. Stable oral liquid compositions of apixaban, methods for their administration, processes for their production, and use of these compositions for treatment of diseases treatable by apixaban are disclosed.

16 Claims, 3 Drawing Sheets

Brief Manufacturing Process Flow Chart

FIG. 1: Preparation of API Phase

FIG. 2: Preparation of povidone solution

FIG. 3: Preparation of final bulk solution

STABLE PHARMACEUTICAL COMPOSITIONS OF APIXABAN

CROSS-REFERENCE TO RELATED APPLICATIONS

This application claims foreign priority to Indian Application No. IN 202241012898, filed on Mar. 9, 2022, which is incorporated herein by reference in its entirety.

FIELD OF THE INVENTION

The present invention relates to liquid pharmaceutical compositions of apixaban or pharmaceutically acceptable salts thereof.

BACKGROUND OF THE INVENTION

Apixaban is an orally active, selective and highly potent inhibitor of coagulation factor Xa (FXa), that directly and reversibly binds to the active site of FXa, and exerts anticoagulant and antithrombotic effects by diminishing the conversion of prothrombin to thrombin. Apixaban is thereby used as an anticoagulant for prophylaxis and treatment of thromboembolic disorders. Chemically, this compound belongs to the class of phenylpiperidines, described as 1-(4-methoxyphenyl)-7-oxo-6-[4-(2-oxopiperidin-1-yl) phenyl]-4,5-dihydropyrazolo [3,4-c] pyridine-3-carboxamide and is represented by the structural formula (I):

Currently, apixaban is marketed in United States under brand name ELIQUIS® (apixaban tablets; 2.5 mg and 5 mg). ELIQUIS® is known to be effective in adults for reducing the risk of stroke and systemic embolism in patients with nonvalvular atrial fibrillation; for the prophylaxis of deep vein thrombosis (DVT), which may lead to pulmonary embolism (PE), in patients who have undergone hip or knee replacement surgery; and for the treatment of DVT and PE, and for the reduction in the risk of recurrent DVT and PE. The recommended maximum dose of ELIQUIS® is 10 mg taken orally twice daily.

Solid dosage forms of apixaban lack the ease of use in persons with dysphagia (difficulty in swallowing). Such patients with dysphagia may delay taking medication or skip the medication entirely, and thus clinicians often seek alternate methods of administration.

The approved pack insert for ELIQUIS® recommends that the tablets need to be crushed and suspended in water, 5% dextrose in water (D5W), or apple juice, or mixed with applesauce and promptly administered via oral route for patients who are unable to swallow whole tablets. Alternatively, the tablets may also be crushed and suspended in 60 mL of water or 5% D5W, and promptly delivered through a nasogastric feeding tube. However, such extemporaneously prepared apixaban formulations are stable only for 4 hours and more importantly such preparations may create compounding or medication errors during administration. Thus, there exists a need for developing ready-to-use, stable, liquid compositions of apixaban, which are suitable for oral administration and which remain stable over extended period of time under suitable storage conditions.

The recommended dose of apixaban ranges from 2.5 mg to 10 mg taken orally twice daily. In the case of treatment of DVT and PE, the recommended dose of apixaban is 10 mg taken orally twice daily for the first 7 days of therapy. After 7 days, the recommended dose is 5 mg taken orally twice daily. This demonstrates that doses of apixaban need to be adjusted to achieve the best clinical outcomes. However, it is difficult to adjust doses using solid dosage forms. The individual dose requirements of patients on apixaban mandates the necessity of a suitable dosage form which is sufficiently flexible to allow accurate dosing and enable optimal dose adjustments for an individual patient's needs. The best way to administer a precisely individualized dose of any drug is through the use of an oral liquid formulation.

Low aqueous solubility (i.e., 0.04 mg/mL) of apixaban is a major hurdle to the development of a liquid formulation of apixaban. It is also reported in the literature that apixaban exhibits poor stability in aqueous solutions due to rapid degradation. There exists a need for developing robust and stable liquid compositions of apixaban, suitable for oral and nasogastric administration, wherein apixaban remains in solubilized state over an extended period of time under suitable storage conditions.

U.S. Pat. No. 9,452,134, discloses oral liquid compositions of apixaban formulated using excipients such as polyethylene glycol, poloxamer and fructose corn syrup, which play a critical role in maintaining the solubility and stability of apixaban in liquid compositions. It is desirable to minimize the use of such excipients for formulating oral solutions, since oral solutions are generally prescribed for treating pediatric population. For pediatric use, it is also desirable to increase the concentration of aqueous solvent in oral solution formulations, in order to minimize the total volume that must be administered.

There is a need to develop more stable and robust apixaban liquid formulations with minimal use of excipients, without compromising on the solubility and stability of the final formulation.

It is desirable to develop novel, stable, ready-to-use liquid compositions of apixaban suitable for oral administration to human subjects, which exhibit prolonged room temperature solubility and stability without any significant loss of potency. The present invention fulfils such need by developing stable oral liquid compositions of apixaban to achieve an improved standard of patient care.

SUMMARY OF THE INVENTION

Specifically, stable liquid pharmaceutical compositions of apixaban for oral administration are provided, wherein the compositions are stable for an extended periods of time. More specifically, stable liquid pharmaceutical compositions of apixaban at concentrations of 0.4 mg/mL or more are provided.

The present invention further relates to stable oral liquid compositions of apixaban, methods for their administration, processes for their production, and use of these compositions for treatment of diseases treatable by apixaban.

The present invention relates to stable liquid pharmaceutical compositions of apixaban or its pharmaceutically acceptable salts thereof, suitable for oral administration for treatment of diseases treatable by apixaban. The inventive apixaban compositions are advantageously stable, ready-to-use (RTU) or ready-to-administer (RTA) and suitable for oral administration.

An aspect of the present invention relates to stable liquid compositions of apixaban, suitable for oral administration, comprising at least one pharmaceutically acceptable solvent, and one or more pharmaceutically acceptable excipients selected from the group comprising solubility enhancing agents, crystallization inhibitors, buffering agents, stabilizers, preservatives, flavoring agents, sweetening agents, and mixtures thereof.

Yet another aspect of the invention relates to stable liquid compositions of apixaban suitable for oral administration, wherein apixaban is present at a concentration of about 0.05 mg/mL to about 5 mg/mL, preferably at a concentration of about 0.4 mg/mL.

The stable liquid compositions of apixaban of the present invention exhibits a pH of about 4.0 to about 8.0, preferably between about 4.5 to about 5.5.

In another aspect, process for preparation of stable liquid pharmaceutical compositions of apixaban suitable for oral administration are provided, wherein the process comprises solubilizing apixaban in a liquid vehicle using solubility enhancing agents along with other pharmaceutically acceptable excipients to obtain a stable solution.

Another aspect of the present invention relates to liquid pharmaceutical compositions of apixaban having extended stability. In an aspect, the present invention relates to stable liquid compositions of apixaban, suitable for oral administration, wherein said compositions are stable for at least 6 months when stored at 40° C./75% RH and 25° C./60% RH conditions.

Another aspect relates to methods of treatment to reduce the risk of stroke and systemic embolism in patients with nonvalvular atrial fibrillation; prophylaxis of deep vein thrombosis (DVT), which may lead to pulmonary embolism (PE), in patients who have undergone hip or knee replacement surgery; treatment of DVT and PE and methods of treatment to reduce the risk of recurrence of DVT and PE; by orally administering an effective amount of a stable liquid pharmaceutical composition of apixaban.

An aspect of the invention relates to a stable oral solution comprising (or consisting of): (i) apixaban at a concentration of about 0.4 mg/mL; (ii) water at a concentration of more than 35% w/w; and (iii) one or more pharmaceutically acceptable excipients, wherein the stable oral solution is stable for at least 6 months at 40° C./75% RH and at 25° C./60% RH. This stable oral solution may further comprise (or consist of) polysorbate at a concentration of less than about 7% w/w of the total solution. Preferably, the stable oral solution is free of polyethylene glycol.

An aspect of the invention relates to a stable oral solution comprising (or consisting of): (i) apixaban at a concentration of about 0.4 mg/mL; (ii) water at a concentration of 35% w/w to 40% w/w; (iii) one or more pharmaceutically acceptable excipients; and (iv) polysorbate at a concentration of 0.1% w/w to 7% w/w of the total solution, wherein the stable oral solution is free of polyethylene glycol; and wherein the stable oral solution is stable for at least 6 months at 40° C./75% RH and at 25° C./60% RH. The stable oral solution may further comprise (v) propylene glycol at a concentration of 30% w/w to 40% w/w; (vi) sodium lauryl sulphate at a concentration of about 0.5% w/w to 2% w/w; and (vii) glycerin at a concentration of about 15% w/w to 25% w/w. Preferably, the stable oral solution may further comprise (viii) povidone at a concentration of about 1% w/w to 10% w/w.

In certain aspects, the above stable oral solutions may have a level of the 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid impurity is less than about 0.5% w/w as determined by HPLC at a wavelength of 270 nm. In certain aspects, the above stable oral solutions may have a level of the 5-((4-(3-carbamoyl-1-(4-methoxy phenyl)-7-oxo-1,4,5,7-tetrahydro-6H-pyrazolo[3,4-c]pyridin-6-yl)phenyl)amino) pentanoic acid impurity is less than about 0.5% w/w as determined by HPLC at a wavelength of 270 nm. In certain aspects, the above stable oral solutions may have a level of the 1-(4-methoxyphenyl)-7-oxo-6-(4-(2-oxopiperidin-1-yl)phenyl)-6,7-dihydro-1H-pyrazolo[3,4-c]pyridine-3-carboxamide impurity is less than about 0.5% w/w as determined by HPLC at a wavelength of 270 nm.

In certain aspects, in the above stable oral solution, the one or more pharmaceutically acceptable excipients are selected from the group consisting of solubility enhancing agents, crystallization inhibitors, buffering agents, stabilizers, preservatives, flavoring agents, sweetening agents, and mixtures thereof.

In certain aspects, the invention also provides a method of treatment to reduce a risk of stroke and systemic embolism in a patient with nonvalvular atrial fibrillation, comprising administering a therapeutically effective amount of the stable oral solution according to claim 1 to a patient in need thereof.

In certain aspects, the invention also provides a method for prophylaxis of deep vein thrombosis (DVT), which may lead to pulmonary embolism (PE), comprising administering a therapeutically effective amount of the stable oral solution according to claim 1 to a patient in need thereof.

In certain aspects, the invention relates to a method wherein the patient is a pediatric or geriatric patient.

By way of non-limiting examples, exemplary combinations applicable to the embodiments described in this application may include any combination with one or more of the elements described above.

DETAILED DESCRIPTION OF THE INVENTION

Unless defined otherwise, all the technical and scientific terms used herein have the same meanings as commonly known by a person skilled in the art. In case of conflict, the definitions provided herein will prevail. Unless specified otherwise, all the percentages, portions and ratios in the present invention are on weight basis.

The terms "about" when used along with a numerical variable, generally means the value of the variable and all the values of the variable within a measurement or an experimental error (e.g., 95% confidence interval for the mean) or within a specified value (e.g., ±10%) within a broader range.

While compositions and methods are described herein in terms of "comprising" various components or steps, the compositions and methods can also "consist essentially of" or "consist of" the various components and steps.

The term "pharmaceutically acceptable" substances mean those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The term "pharmaceutically acceptable salt" refers to apixaban salts which are formed with inorganic or organic acids.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

The terms "pharmaceutical composition", "pharmaceutical product", "pharmaceutical dosage form", "dosage form", "composition", "formulation", etc., refer to a pharmaceutical composition administered to a patient in need of treatment, including but not limited to tablet, hard-gelatin capsule, soft-gelatin capsule, oral suspension, oral solution, enteric coated hard-gelatin capsule, enteric coated soft-gelatin capsule, coated cores, pellets, micro pellets, pills, compressed tablets, granules, spheres, capsules and the like.

The terms "liquid pharmaceutical composition," refer to a pharmaceutical composition administered to a patient, including solution or suspension.

The term "ready-to-use," as used herein, refers to a formulation that does not require constitution or dilution with a prescribed amount of diluent, e.g., purified water or other suitable diluent, before use by the designated route.

The term "ready-to-administer" as used herein, refers to a formulation that does not require any steps or handling or manipulation before administration and can be directly administered orally to the patient.

The terms "ready-to-use" and "ready-to-administer" can be used interchangeably. The present application relates to stable ready-to-administer (RTA) or ready-to-use (RTU) apixaban compositions suitable for oral administration comprising apixaban and one or more pharmaceutically acceptable excipient.

The terms "dosage", "dose unit" or "dose" as used herein means amount of pharmaceutical formulation comprising therapeutically active agent(s) administered at a time.

By "effective amount" or "therapeutically effective amount" is meant the amount of a drug sufficient to treat, prevent, or ameliorate a condition in a subject or patient. The effective amount of apixaban or pharmaceutically acceptable salt thereof, may be determined and adjusted by a person of ordinary skill to provide the appropriate amount and dosage regimen, e.g., depending upon manner of administration, the age, body weight, sex, and/or general health of the patient.

Within the context of this invention, the term "solution" refers to a mixture of one or more substances dispersed molecularly (i.e., dissolved) in a dissolving liquid medium or vehicle. The solution is preferably homogeneous, in the sense that Active Pharmaceutical Ingredient (API) is essentially uniformly dissolved and distributed in the solution.

The term "solubility" means solubility of apixaban or its pharmaceutically acceptable salts in media such as water, alcohols, oils, surfactants, solubilizers, polyols, buffer, gastrointestinal simulated fluid, gastrointestinal fluid and the like.

The term "subject" refers to an animal, including a human or non-human. The terms patient and subject may be used interchangeably herein.

The terms "stable" and "stability" mean that the evolution of the product with time and/or under specific environmental conditions (i.e., temperature, humidity, etc.) has no significant effects on its quality, safety and/or efficacy for a given time period. It can be measured through the formation of degradation products (impurities), variation of pH, appearance (precipitation), microbial growth, and/or color. The term "stable" may indicate physical stability or chemical stability.

The term "physically stable" means a solution of apixaban with no visible apixaban crystals and with no tendency to precipitate upon storage at 25° C./60% RH or at 40° C./75% RH for a time period of at least 1 month, 2 months, 6 months, 12 months, 18 months, 24 months or 36 months.

The term "chemically stable" means that no more than 10% loss of apixaban under typical commercial storage conditions. Preferably, formulations of the present invention will have no more than about 8% loss of apixaban, more preferably, no more than about a 5% loss of apixaban, more preferably, no more than about a 3% loss of apixaban under typical commercial storage conditions (i.e., at 25° C./60% RH or at 40° C./75% RH) for at least 2 months, for at least 3 months, at least 6 months, at least 9 months, at least 12 months, at least 15 months, at least 18 months, at least 21 months, at least 24 months, at least 30 months and at least 36 months.

The term "any person" refers to any human being capable of administering dose of apixaban composition to a patient, wherein human being includes physicians, healthcare professionals, nurse, pharmacist, pharmacy technicians and patient.

As used herein, "prolonged duration" refers to the holding of a composition under controlled or uncontrolled conditions for a period of more than 30 days.

As used herein, "significant loss of potency" can mean as no more than about a 10% loss of apixaban under typical commercial storage conditions.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition;

preventing spread of disease, disorder, or condition; delay or slowing the progress of the disease, disorder, or condition; amelioration or palliation of the disease, disorder, or condition; and remission (whether partial or total), whether detectable or undetectable.

The present application relates to stable liquid pharmaceutical compositions of apixaban, wherein apixaban is present at a concentration of 0.05 mg/mL or more. In one aspect, pharmaceutical composition of the present invention comprises apixaban, wherein the concentration of apixaban in the composition is 0.4 mg/mL.

In a preferred embodiment, concentration of apixaban in the inventive composition is about 0.05 mg/mL, about 0.1 mg/mL, about 0.2 mg/mL, about 0.3 mg/mL, about 0.4 mg/mL, about 0.5 mg/mL, about 1.0 mg/mL, about 5.0 mg/mL, 10.0 mg/mL, about 20 mg/mL, about 30 mg/mL, about 40 mg/mL or about 50 mg/mL. The concentration of apixaban may be from about 0.05 mg/mL to about 50 mg/mL, from about 0.1 mg/mL to about 40 mg/mL, from about 0.2 mg/mL to about 40 mg/mL, from about 0.3 mg/mL to about 30 mg/mL, from about 0.3 mg/mL to about 20 mg/mL, from about 0.4 mg/mL to about 10 mg/mL or from about 0.4 mg/mL to about 1 mg/mL.

Preferably, the liquid pharmaceutical composition will be provided in a dosage form that is suitable for oral administration, including but not limited to a solution, suspension, syrup, or elixir. The pharmaceutical compositions may be formulated according to conventional pharmaceutical practice.

Another embodiment provides methods of treatment to reduce the risk of stroke and systemic embolism in patients with nonvalvular atrial fibrillation; prophylaxis of deep vein thrombosis (DVT), which may lead to pulmonary embolism (PE), in patients who have undergone hip or knee replacement surgery; treatment of DVT and PE and methods of treatment to reduce the risk of recurrence of DVT and PE, by orally administering to a subject from about 0.05 mg/mL to about 5 mg/mL of stable liquid pharmaceutical composition comprising apixaban, at least one pharmaceutically acceptable liquid vehicle and one or more pharmaceutically acceptable excipients.

As used herein the term "apixaban" refers to apixaban free base or its pharmaceutically acceptable salts, solvates or hydrates thereof. In principle, any crystalline form or amorphous form of apixaban may be used for manufacturing inventive pharmaceutical compositions of the present invention.

In an embodiment, the present invention provides stable liquid pharmaceutical composition suitable for oral administration, wherein the composition comprises (i) apixaban, (ii) at least one pharmaceutically acceptable liquid vehicle, and (iii) one or more pharmaceutically acceptable excipients.

In another embodiment, the present invention provides stable liquid pharmaceutical composition suitable for oral administration, wherein the composition comprises (i) apixaban as the sole active ingredient, (ii) at least one pharmaceutically acceptable liquid vehicle, and (iii) one or more pharmaceutically acceptable excipients The terms "liquid vehicle" or "pharmaceutically acceptable liquid vehicle" or "solvent" or "pharmaceutically acceptable solvent" as used herein, is any liquid medium used for dilution or dissolution of oral or peroral formulations, such as water, aqueous organic solvents, non-aqueous organic solvents and other liquids described herein or used in the pharmaceutical and/or food industry. The liquid vehicle of the present invention is selected from water, glycerin, alcohol, propylene glycol, ethanol, glycerin, dimethylacetamide, N-methyl-pyrrolidone, dimethyl sulfoxide, or their mixtures thereof. Preferably, purified water, glycerin and propylene glycol are used as liquid vehicles.

In an embodiment the inventive composition comprises water at a concentration of more than about 30% (w/w), more than about 31% (w/w), more than about 32% (w/w), more than about 33% (w/w), more than about 34% (w/w), more than about 35% (w/w), more than about 36% (w/w), more than about 37% (w/w), more than about 38% (w/w), more than about 39% (w/w), more than about 40% (w/w), more than about 41% (w/w), more than about 42% (w/w), more than about 43% (w/w), more than about 44% (w/w), more than about 45% (w/w), more than about 46% (w/w), more than about 47% (w/w), more than about 48% (w/w), more than about 49% (w/w), more than about 50% (w/w), more than about 55% (w/w), more than about 60% (w/w) of water of the total composition.

In another embodiment the inventive composition comprises water at a concentration range of from about 30% (w/w) to about 60% (w/w) of the total composition, from about 30% (w/w) to about 55% (w/w) of the total composition, from about 30% (w/w) to about 50% (w/w) of the total composition, from about 30% (w/w) to about 45% (w/w) of the total composition, from about 30% (w/w) to about 40% (w/w) of the total composition, from about 30% (w/w) to about 35% (w/w) of the total composition, from about 35% (w/w) to about 50% (w/w) of the total composition, from about 35% (w/w) to about 45% (w/w) of the total composition, from about 35% (w/w) to about 40% (w/w) of the total composition.

The concentration of glycerin and propylene glycol in the inventive composition ranges from about 5% to 80%, preferably 10% to 70%, more preferably 15% to 60%, based on total weight of the composition.

In another embodiment, the present invention provides stable liquid pharmaceutical compositions suitable for oral administration comprising (i) apixaban at a concentration of about 0.4 mg/mL; (ii) at least one pharmaceutically acceptable liquid vehicle; and (iii) optionally one or more pharmaceutically acceptable excipients selected from the group comprising solubility enhancing agents, crystallization inhibitors, buffering agents, stabilizers, preservatives, flavoring agents, sweetening agents, and mixtures thereof.

The formulation of the present invention may optionally include an antioxidant, acidifying agent, alkalizing agent, bulking agent, complexing agent, cryoprotectant, chelating agent, density modifier, electrolyte, plasticizers, volatility modifier, viscosity modifier, coloring agents, other excipients known by those of ordinary skill in the art for use in pharmaceutical formulations.

In an embodiment, the present invention provides stable oral solution comprising (i) apixaban at a concentration of about 0.4 mg/mL; (ii) at least one pharmaceutically acceptable liquid vehicle; and (iii) one or more other pharmaceutically acceptable excipients selected from the group comprising solubility enhancing agents, crystallization inhibitors, buffering agents, stabilizers, preservatives, flavoring agents, sweetening agents, and mixtures thereof, wherein the solution has a pH in the range of about 4.5 to about 5.5.

Apixaban is a poorly water-soluble compound with non-ionizable functional groups. It has low aqueous solubility of 40-50 μg/mL in water with a pH independent solubility profile. Its solubility is very low throughout physiological pH range of 1.0-8.0. A solubility-enhancing agent is a compound, or compounds, that enhance(s) the solubility of apixaban. Suitable solubility enhancing agents include one or more surfactants, hydrophilic polymers, polyhydric alcohols, cyclodextrins or mixtures thereof. In a preferred embodiment, concentration of the solubility enhancing agent ranges from about 0.1% to 80%, based on total weight of the composition.

Suitable surfactants used in the present invention may be ionic or non-ionic surface-active agents. Suitable ionic surfactants include, but are not limited to, those containing carboxylate, sulfonate and sulfate ions. Examples of anionic surfactants include sodium, potassium, ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate; quaternary ammonium compounds such as benzalkonium chloride, benzethonium chloride, cetrimonium bromide, stearyl dimethylbenzyl ammonium chloride, polyoxyethylene. In a preferred embodiment, the concentration of ionic surfactant ranges from about 0.05% to 5%, based on total weight of the composition.

Suitable nonionic surfactants include, but not limited to, glycol stearates such as ethylene glycol monostearate, propylene glycol myristate, glyceryl monostearate, glyceryl stearate, polyglyceryl-4-oleate, sorbitan acylate, sucrose acylate, polyethylene glycol dilaurate, polyethylene glycol monolaurate, polysorbates, polyoxyethylene octylphenylether, polyethylene glycol cetyl ether, polyoxyethylene tridecyl ether, polypropylene glycol butyl ether, stearoyl monoisopropanolamide, polyoxyethylene hydrogenated tallow amide, polyoxyl-ethylated castor oils (CREMOPHOR®), polyoxyethylene esters of 12-hydroxystearic acid (SOLUTOL®) and PEGylated glycerides (LABRASOL®). In a preferred embodiment, the concentration of non-ionic surfactant ranges from about 0.05% to 2%, based on total weight of the composition. In another embodiment polysorbate is the preferred non-ionic surfactant, at a concentration of less than 7% (w/w) of the total composition, less than 6% (w/w) of the total composition, less than 5% (w/w) of the total composition, less than 4% (w/w) of the total composition, less than 3% (w/w) of the total composition, less than 2% (w/w) of the total composition, less than 1% (w/w) of the total composition.

A hydrophilic polymer as referred to herein is a compound of high molecular weight derived by the addition of many smaller units and which has a strong affinity for water. Suitable hydrophilic polymers can be selected from the group consisting of povidone, hydroxypropyl cellulose, or hydroxypropyl methylcellulose. In a preferred embodiment, the concentration of hydrophilic polymer ranges from about 0.5% to 20%, based on total weight of the composition.

A polyhydric alcohol as referred to herein is a compound with more than one hydroxyl group. Non-limiting examples of polyhydric alcohols that can be used are glycerin, propylene glycol, and mannitol. In a preferred embodiment, the concentration of polyhydric alcohol ranges from about 5% to 80%, based on total weight of the composition.

The cyclodextrins can be selected from the group consisting of α-cyclodextrin, β-cyclodextrin, δ-cyclodextrin, γ-cyclodextrin or their derivatives. In a preferred embodiment, the concentration of cyclodextrins ranges from about 5% to 80%, based on total weight of the composition.

Concentration of apixaban of 0.4 mg/mL in an oral liquid formulation adequately supports a desired dosage range of 0.04 mg to 5.0 mg with acceptable volumes ranging, for example, between 0.10 mL and 12.5 mL, which can be accurately measured and conveniently administered in the target patient population. Extensive solubility studies were conducted to identify a vehicle/solubilizer that supports the 0.4 mg/mL concentration. A minimum solubility of apixaban of at least 0.50 mg/mL at room temperature (15-25° C.) can provide a robust formulation at the 0.4 mg/mL target concentration. Since it is preferable for the apixaban oral liquid formulation in accordance with the present invention to be suitable for ambient storage, this solubility helps to maintain apixaban in a dissolved state within the range of temperatures to which the formulation may be exposed during shipping and handling by the patients.

Apixaban saturation solubility study data, as tabulated below, illustrates the best possible solubilizing agents that are utilized in the present invention.

TABLE 1

Saturation solubility of apixaban

| S. No. | Solubility enhancing agents | *mg/g |
|---|---|---|
| 1 | Glycerine | 0.33 |
| 2 | Propylene glycol | 1.45 |
| 3 | PEG-400 | 2.92 |
| 4 | Polysorbate-80 | 0.98 |
| 5 | Glycerine + Propylene glycol (60:40) | 0.85 |
| 6 | Glycerine + PEG-400 (80:20) | 0.3 |
| 7 | Glycerine + Polysorbate-80 (80:20) | 0.41 |
| 8 | PEG-400 + Polysorbate-80 (40:60) | 1.94 |
| 9 | Labrasol ® ALF | 1.55 |
| 10 | Kolliphor ® EL | 0.56 |
| 11 | Sodium lauryl sulphate (6.66% solution in Purified water) | 4.18 |
| 12 | Povidone K 30 (6.66% solution in Purified water) | 0.17 |

*Quantity of apixaban dissolved per gram of solubility enhancing agent

The present invention involves the use of a solubility enhancing agent for solubilization of the active ingredient (i.e., apixaban). However, apixaban may crystallize over time resulting in loss of desired properties and shortened shelf life. The present invention uses "crystallization inhibitors" in order to promote the physical stability of apixaban in liquid formulations. The term "crystallization inhibitors" as used herein, inhibits the crystallization of active ingredient thereby making the formulation physically stable for a longer period of time. For example, polyvinylpyrrolidone (KOLLIDON®), polyvinyl alcohol, hydroxypropyl cellulose, hydroxypropyl methylcellulose, ethyl cellulose, gelatin, starch (derivatives), dextrins and dextrans, such as, for example, α-, β- and γ-cyclodextrin, dimethyl-βcyclodextrin and 2-hydroxypropyl-β-cyclodextrin), sterols (such as cholesterol) or bile acids (such as cholic acid or lithocholic acid) can be used. The preferred crystallization inhibitors in the present invention are polyvinylpyrrolidones and hydroxypropyl methylcellulose. In a preferred embodiment, the concentration of crystallization inhibitors ranges from about 0.5% to 20%, based on total weight of the composition.

The pharmaceutical composition of the present invention may contain a "stability enhancing agent" or "stabilizer". The terms "stability enhancing agent" or "stabilizer" as used herein inhibits, prevents, slows down, or reduces the degradation of apixaban. More specifically, stability enhancing agents include amino acids such as glycine, alanine, glutamate, sodium glutamate, L-arginine, lysine, L-cysteine or methionine; sodium chloride or sodium sulfate salts; ethylenediaminetetraacetic acid (EDTA), metal ions such as zinc, magnesium and calcium or mixtures thereof; natural or synthetic gums, cellulosic derivatives such as carboxy methyl cellulose, ethyl cellulose, hydroxyethyl cellulose, hydroxyl propyl cellulose, hydroxyl propyl methylcellulose, methyl cellulose, polyanionic cellulose; cyclodextrins; sugars; sugar alcohols; monosaccharides, disaccharides or polysaccharides or combinations thereof. The concentration of stabilizer ranges from 0.001% to 20%, based on total weight of the composition.

The pH of the inventive composition ranges from about 3 to about 8. In some embodiments, pH of the composition is preferably between 4.0 to 6.0, more preferably between about 4.5 to about 5.5. The pharmaceutical compositions of the present invention may contain a buffer, to resist change in pH upon dilution or addition of acid or alkali. Such compounds include, by way of example and without limitation, sodium dihydrogen phosphate monohydrate, disodium hydrogen phosphate anhydrous, citric acid, ascorbic acid, acetic acid, sodium acetate, adipic acid, benzoic acid, sodium benzoate, sodium citrate, monobasic sodium phosphate, dibasic sodium phosphate, disodium hydrogen phosphate dodecahydrate, lactic acid, tris buffer, tartaric acid, potassium metaphosphate, potassium phosphate, monobasic sodium acetate, sodium bicarbonate, sodium ascorbate anhydrous, sodium ascorbate monohydrate, sodium tartrate and others known to those of ordinary skill in the art. The concentration of buffer in the present invention ranges from 0.001% to 10%, based on total weight of the composition.

The pH of the composition can be adjusted with any combination of acidic and/or basic pH adjusting agents known in the art. Acidic materials include organic acids and inorganic acids, in particular, monocarboxylic acids, dicarboxylic acids, and tricarboxylic acids, for example, acetic acid, citric acid, tartaric acid, alpha-hydroxy acids, beta-hydroxy acids, salicylic acid, lactic acid, malic acid, glycolic acid, amino acids and natural fruit acids, or inorganic acids, for example, hydrochloric acid, nitric acid, sulfuric acid, sulfamic acid, phosphoric acid, and combinations thereof. Basic materials include inorganic and organic bases, and combinations thereof. Examples of inorganic bases include but are not limited to the alkali metal hydroxides (especially sodium, potassium, and ammonium), and alkali metal salts such as sodium borate (borax), sodium phosphate, sodium pyrophosphate, and the like; and mixtures thereof. Examples of organic bases include triethanolamine (TEA), diisopropanolamine, triisopropanolamine, aminomethyl propanol, dodecylamine, cocamine, oleamine, morpholine, triamylamine, triethylamine, tetrakis (hydroxypropyl) ethylenediamine, L-arginine, aminomethyl propanol, tromethamine (2-amino 2-hydroxymethyl-1,3-propanediol), and PEG-15 cocamine. Such pH adjusters may be present at a concentration that ranges from 0.001% to 20%, based on total weight of the composition.

In addition to stabilizing pharmaceutical preparations against chemical and physical degradation, liquid preparations, especially multi-dose preparations, must usually be protected from microbial contamination. In one embodiment, pharmaceutical composition of the present invention may optionally comprise a preservative selected from the group consisting of benzoic acid and the sodium or potassium salts thereof, ethanol, isopropanol, methanol, butyl alcohol, benzalkonium chloride, benzethonium chloride, benzyl alcohol, butylparaben, cetylpyridinium chloride, chlorobutanol, chlorocresol, cresol, dehydroacetic acid, ethylparaben, ethylparaben sodium, methylparaben, methylparaben sodium, phenol, phenylethyl alcohol, phenylmercuric acetate, phenylmercuric nitrate, potassium benzoate, potassium sorbate, propylparaben, propylparaben sodium, sodium dehydroacetate, sodium propionate, sorbic acid, thimerosal, thymol, or combinations thereof. The concentration of preservative ranges from 0.001% to 10%, based on total weight of the composition.

The term "sweetening agents" refers to both bulk (caloric) and intense (non-caloric) sweeteners, which impart sweet taste to the preparation. Examples of sweeteners are acesulfame, alitame, aspartame, cyclamate, saccharin, sucralose, acesulfame potassium or sodium cyclamate, and mixtures thereof. In particular, the sweetening agent is sucralose. The concentration of sweetener ranges from 0.001% to 10%, based on total weight of the composition The term "flavoring agent," as used herein, refers to an agent or a mixture of agents that adds flavor to a mixture. Flavoring agent is selected from the group consisting of a natural flavor, an artificial flavor, and mixtures thereof. Flavoring agents include, but are not limited to, mint, peppermint, cola, apple, vanilla, orange, peach, apricot, raspberry, cherry, honey, lemon, coconut, pineapple, strawberry banana, mixed berry, mixed red fruit and cream flavors and mixture thereof. In particular, the flavoring agent is orange flavor. The concentration of flavoring agent ranges from 0.001% to 10%, based on total weight of the composition.

In one embodiment, the present invention provides stable polyethylene glycol-free oral solution comprising (i) apixaban at a concentration of about 0.4 mg/mL; (ii) at least one pharmaceutically acceptable liquid vehicle; (iii) one or more pharmaceutically acceptable excipients.

In another embodiment, the present invention provides stable carbohydrate-free oral solution comprising (i) apixaban at a concentration of about 0.4 mg/mL; (ii) at least one pharmaceutically acceptable liquid vehicle; (iii) one or more pharmaceutically acceptable excipients.

In yet another embodiment, the present invention provides stable oral solution comprising (i) apixaban at a concentration of about 0.4 mg/mL; (ii) purified water; (iii) one or more pharmaceutically acceptable excipients, wherein the quantity of purified water in the composition ranges from about 30% (w/w) to about 40% (w/w).

In yet another embodiment, the present invention provides stable oral solution comprising (i) apixaban at a concentration of about 0.4 mg/mL; (ii) purified water; (iii) one or more pharmaceutically acceptable excipients, wherein the quantity of purified water in the composition ranges from about 30% (w/w) to about 40% (w/w).

In an embodiment, the present invention provides a process for preparation of a stable, liquid pharmaceutical formulation of apixaban for oral administration, wherein the process comprises; Phase 1) preparation of API phase, as provided in FIG. 1; Phase 2) preparation of povidone solution, as provided in FIG. 2 and Phase 3) preparation of final bulk solution, as provided in FIG. 3.

In an embodiment, the pharmaceutical composition of present invention is filled into suitable pharmaceutically acceptable containers selected from the group consisting of bottles, bags and vials.

In an embodiment, the pharmaceutically acceptable container is a bottle, wherein the bottle is selected from group consisting of glass bottle or plastic bottle, wherein glass bottle is selected from group consisting of Type I, II and III borosilicate glass bottles, wherein the glass bottle may be amber color glass bottle or clear glass bottle.

In another embodiment, the pharmaceutically acceptable container is a bottle, wherein the bottle is selected from group consisting of high-density polyethylene (HDPE) bottle, polyethylene terephthalate (PET) and polypropylene (PP), wherein the plastic bottle may be amber color, white opaque or translucent plastic bottle.

In a preferred embodiment, the glass and HDPE bottles will be available in 30, 60, 100, 120, 150, 250 & 500 mL fill volumes.

In an embodiment, the pharmaceutical composition of present application was packed in a kit comprising bottle with child resistant cap, dosing syringe, adapter and dosing syringe.

Stability

As used herein, the term "stable" is defined as no more than about 10% loss of apixaban under typical commercial storage conditions. In certain embodiments, the compositions of the present invention, wherein the loss of apixaban is no more than about 5%, no more than about 4%, no more than about 3% loss, no more than about 2% loss, no more than about 1% loss, under typical commercial storage conditions. The composition retains at least about 90% of the potency of apixaban, as determined by HPLC at a wavelength of 278 nm, after storing the composition at 40° C./75% RH for at least 6 months. In certain aspects, the composition retains at least about 95% of the potency of apixaban, as determined by HPLC at a wavelength of 278 nm, after storing at 25° C./60% RH for at least twelve months.

In an embodiment, the present invention provides stable oral solution comprising (i) apixaban, (ii) at least one pharmaceutically acceptable liquid vehicle, (iii) one or more pharmaceutically acceptable excipients, wherein the solution is stable for at least 6 months at 40° C./75% RH.

In an embodiment, the present invention provides stable oral solution comprising (i) apixaban; (ii) at least one pharmaceutically acceptable liquid vehicle; and (iii) one or more pharmaceutically acceptable excipients, wherein the solution is stable for at least 12 months at 25° C./60% RH.

Apixaban has known as well as unknown impurities. In particular, 0-desmethoxy impurity, amino acid impurity, acid impurity, chloro impurity, ester impurity and methyl ester impurity were monitored.

TABLE 2

Potential impurities for Apixaban

| S. No | Impurity Name | Type | Structure | Chemical Name |
|---|---|---|---|---|
| 1. | Acid Impurity | Process/ Degradation | | 1-(4-methoxyphenyl)-7-oxo-6-(4-(2-oxopiperidin-1-yl)phenyl)-4,5,6,7-tetrahydro-1H-pyrazolo [3,4-c] pyridine-3-carboxylic acid |
| 2. | Amino Acid Impurity | Process/ Degradation | | 5-((4-(3-Carbamoyl-1-(4-methoxy phenyl)-7-oxo-1,4,5,7-tetrahydro-6H-pyrazolo[3,4-c]pyridin-6-yl)phenyl)amino) pentanoic acid |
| 3. | Dehydro Impurity | Process/ Degradation | | 1-(4-Methoxyphenyl)-7-oxo-6-(4-(2-oxopiperidin-1-yl)phenyl)-6,7-dihydro-1H-pyrazolo[3,4-c]pyridine-3-carboxamide |

TABLE 2-continued

Potential impurities for Apixaban

| S. No | Impurity Name | Type | Structure | Chemical Name |
|---|---|---|---|---|
| 4. | Chloro Impurity | Process | | 1-(4-Chlorophenyl)-7-oxo-6-(4-(2-oxo piperidin-1-yl)phenyl)-4,5,6,7-tetrahydro-1H-pyrazolo [3,4-c]pyridine-3-carboxamide |
| 5. | Methyl Ester Impurity | Process | | methyl 1-(4-methoxyphenyl)-7-oxo-6-(4-(2-oxopiperidin-1-yl)phenyl)-4,5,6,7-tetrahydro-1H-pyrazolo [3,4-c]pyridine-3-carboxylate |
| 6. | Ester Impurity | Process | | ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate |

In an embodiment, the present invention provides stable oral solution comprising (i) apixaban at a concentration of 0.4 mg/mL; (ii) at least one pharmaceutically acceptable vehicle; and (iii) one or more other pharmaceutically acceptable excipients, wherein the level of total impurities in the composition is less than about 5% (w/w), preferably less than about 3% (w/w), more preferably less than about 1% (w/w), more preferably less than about 0.5% (w/w) as determined by HPLC at a wavelength of 270 nm.

In another embodiment, the level of any unknown impurities in the inventive composition resulting from the degradation of apixaban is less than about 5% (w/w), preferably less than about 3% (w/w), preferably less than about 1% (w/w), preferably less than about 0.5% (w/w), preferably less than about 0.15% (w/w) and more preferably less than about 0.1% (w/w) as determined by HPLC at a wavelength of 270 nm.

In yet another embodiment, the level of known impurities in the inventive composition resulting from the degradation of apixaban is less than about 5% (w/w), preferably less than about 3% (w/w), preferably less than about 1% (w/w), preferably less than about 0.5% (w/w), preferably less than about 0.15% (w/w) and more preferably less than about 0.1% (w/w) as determined by HPLC at a wavelength of 270 nm.

Analysis of Samples Withdrawn During Chemical Analysis of Apixaban

The samples withdrawn were analyzed for drug content using the following HPLC procedure. The materials and general conditions are listed below:

TABLE 3

Chromatographic conditions (Drug content analysis)

| | |
|---|---|
| Chromatographic Mode | HPLC system equipped with UV/PDA detector |
| Column | L1, 4.6 × 150 mm, 2.7 μm; |

TABLE 3-continued

Chromatographic conditions (Drug content analysis)

| Wavelength | Methylparaben: 256 nm |
| --- | --- |
| | Propylparaben: 256 nm |
| | Apixaban: 278 nm |
| Flow rate | 0.8 mL/minute |
| Injection volume | 15 μL |
| Column temperature Temperature | 30° C. |
| Sample temperature | 25° C. |
| Run time | 30 minutes |
| Mobile Phase A | Buffer (pH 2.5, 20 mM phosphate buffer) solution and acetonitrile in the ratio of 70:30 (% v/v). |
| Mobile Phase B | Buffer (pH 2.5, 20 mM phosphate buffer) solution and acetonitrile in the ratio of 30:70 (% v/v). |
| Mode of Elution | Gradient |

| Time | Mobile Phase-A (%) | Mobile Phase-B (%) |
| --- | --- | --- |
| 0 | 100 | 0 |
| 13 | 100 | 0 |
| 20 | 0 | 100 |
| 24 | 0 | 100 |
| 25 | 100 | 0 |
| 30 | 100 | 0 |

The samples withdrawn were analyzed for related substances using the following HPLC procedure. The materials and general conditions are listed below:

TABLE 4

Chromatographic conditions (Related substance analysis)

| Chromatographic Mode | HPLC system equipped with UV/PDA detector |
| --- | --- |
| Column | L11, 250 × 4.6 mm, 5μ |
| Wavelength | 270 nm |
| Flow rate | 1.0 mL/minute |
| Injection volume | 40 μL |
| Column temperature Temperature | 40° C. |
| Sample temperature | 25° C. |
| Run time | 65 minutes |
| Mobile Phase A | Buffer (pH 5.5, 30 mM acetate buffer) solution and acetonitrile in the ratio of 90:10 (% v/v). |
| Mobile Phase B | Buffer (pH 5.5, 30 mM acetate buffer) solution and acetonitrile in the ratio of 10:90 (% v/v). |
| Mode of Elution | Gradient |

| Time | Mobile Phase-A (%) | Mobile Phase-B (%) |
| --- | --- | --- |
| 0 | 100 | 0 |
| 5 | 100 | 0 |
| 15 | 85 | 15 |
| 25 | 70 | 30 |
| 35 | 60 | 40 |
| 45 | 50 | 50 |
| 55 | 40 | 60 |
| 55.5 | 100 | 0 |
| 65 | 100 | 0 |

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1

Apixaban compositions were set forth in Table 5

TABLE 5

Compositions to study effect of crystallization inhibitors

| | | Composition (mg/mL) | |
| --- | --- | --- | --- |
| S. No. | Ingredients | A1 | A2 |
| 1 | Apixaban | 0.40 | 0.40 |
| 2 | Propylene Glycol | 367.61 | 438.62 |
| 3 | Polysorbate 80 | 8.30 | 8.30 |
| 4 | Povidone K 25 | 46.96 | — |
| | Hydroxypropyl methyl cellulose (HPMC E5) | — | 10.00 |
| 5 | Sodium lauryl sulphate | 12.00 | 12.00 |
| 6 | Methyl paraben | 0.91 | 2.36 |
| 7 | Propyl Paraben | 0.10 | 0.23 |
| 8 | Glycerine | 234.75 | 234.75 |
| 9 | Fructose Corn Syrup | 234.75 | — |
| 10 | Citric Acid anhydrous | 0.15 | 0.15 |
| 11 | Sodium citrate dihydrate | 0.07 | 0.07 |
| 12 | Sucralose | 4.71 | 4.71 |
| 13 | Orange Flavour | 2.88 | — |
| 14 | Purified water | 263.41 | 463.41 |
| | Total | 1177.0 | 1175.0 |

Manufacturing Procedure of Compositions A1 and A2:

Propylene glycol, Polysorbate 80 and purified water were mixed together in a suitable container. Sodium lauryl sulfate and povidone/hydroxypropyl methyl cellulose was added to above solution and mixed continuously at room temperature. Methyl paraben and propyl paraben were added and stirred continuously. The solution was heated under continuous stirring at 60° C.±2° C. and apixaban was added under continuous stirring until a clear solution is formed. Temperature of above solution was brought to room temperature under continuous stirring. Glycerin, sweetener and buffering agents were added under continuous stirring. Final solution was filtered to get a clear solution.

Freeze thaw cycle study: Above compositions were subjected to FTC study, wherein 5 cycles of FTC were carried out at −20° C. and Room Temperature for 24 hours each.

TABLE 6

Initial and stability analysis data with povidone

Composition A1

| Parameters | Initial | 1 W 60° C. | 2 W 60° C. | 1 M 40° C./75% RH | 2 M 40° C./75% RH | 3 M 40° C./75% RH | 1 M 25° C./60% RH | 3 M 25° C./60% RH |
|---|---|---|---|---|---|---|---|---|
| Description | Clear pale yellow colour solution | | | | | | | |
| pH | 4.65 | 4.46 | 4.25 | 4.23 | 4.26 | 4.28 | 4.43 | 4.42 |
| API Assay | 101.2 | 102.0 | 101.2 | 103.7 | 102.6 | 100.8 | 103.6 | 102.1 |
| Methyl paraben | 101.9 | 102.1 | 103.1 | 102.8 | 102.4 | 101.5 | 103.6 | 102.3 |
| Propyl paraben | 101.4 | 101.8 | 102.1 | 103.5 | 102.4 | 101.4 | 103.3 | 102.1 |
| Related Substance (% w/w) | | | | | | | | |
| Dehydro Imp. | ND | ND | ND | ND | ND | ND | ND | ND |
| Amino acid Imp. | ND | ND | 0.11 | ND | 0.07 | 0.07 | ND | 0.03 |
| Acid Imp. | ND | 0.02 | 0.03 | 0.01 | ND | 0.02 | ND | ND |
| Chloro Imp. | ND | 0.04 | ND | ND | 0.02 | 0.01 | ND | 0.02 |
| Methyl ester Imp. | 0.05 | 0.03 | 0.03 | 0.05 | 0.05 | 0.04 | 0.05 | 0.04 |
| Ester Imp. | ND | ND | ND | ND | ND | ND | ND | ND |
| SMUI (RRT 1.04) | 0.04 | 0.04 | 0.14 | 0.03 | 0.1 | 0.08 | 0.03 | 0.05 |
| Total | 0.13 | 0.2 | 0.42 | 0.17 | 0.39 | 0.43 | 0.12 | 0.22 |

TABLE 7

Initial and stability analysis data with HPMC

Composition A2

| Parameters | Initial | 1 W 60° C. | 2 W 60° C. | 1 M 40° C./75% RH | 2 M 40° C./75% RH | 3 M 40° C./75% RH | 3 M 25° C./60% RH |
|---|---|---|---|---|---|---|---|
| Description | Clear, colorless solution | | | | | | |
| Methyl paraben | 103.1 | 103.3 | 101.5 | 101.7 | 101.5 | 101.0 | 100.6 |
| Propyl paraben | 102.6 | 102.8 | 102.7 | 102.4 | 101.9 | 102.2 | 101.5 |
| Assay | 101.7 | 102.3 | 103.2 | 102.4 | 100.9 | 101.4 | 101.4 |
| pH | 4.87 | 4.78 | 4.74 | 4.80 | 4.84 | 4.79 | 4.84 |
| Related Substance (% w/w) | | | | | | | |
| dehydro Imp. | ND | ND | ND | ND | ND | ND | ND |
| Amino acid Imp. | ND | ND | ND | ND | ND | 0.05 | 0.03 |
| Acid Imp. | ND | ND | ND | ND | 0.05 | ND | ND |
| Chloro Imp. | ND | ND | ND | 0.03 | ND | 0.02 | 0.02 |
| Methyl ester Imp. | 0.04 | 0.04 | ND | 0.06 | 0.02 | 0.04 | 0.04 |
| Ester Imp. | ND | ND | ND | ND | 0.05 | ND | 0.01 |
| SMUI (RRT 1.04) | 0.04 | 0.05 | 0.04 | 0.04 | 0.03 | 0.04 | 0.04 |
| Total | 0.14 | 0.12 | 0.08 | 0.15 | 0.23 | 0.21 | 0.22 |

Observation: The Compositions A1 and A2 are both physically and chemically stable for at least 3 months at 40° C./75% RH condition, without visible particles and with no significant change in assay and impurity profile. No precipitation was observed at the end of five cycles of FTC study.

Example 2: Effect of pH on Stability of Apixaban Oral Solution

Apixaban compositions were set forth in Table 8

TABLE 8

Compositions to study effect of pH

| S. No. | Ingredients | B1 | B2 | B3 | B4 | B5 |
|---|---|---|---|---|---|---|
| 1 | Apixaban | | | 0.400 | | |
| 2 | Propylene Glycol | | | 366.92 | | |
| 3 | Polysorbate 80 | | | 8.30 | | |
| 4 | Povidone K 25 | | | 46.96 | | |
| 5 | Sodium lauryl sulphate | | | 12.00 | | |
| 6 | Purified water | | | 263.41 | | |
| 7 | Methyl paraben | | | 2.352 | | |
| 8 | Propyl Paraben | | | 0.235 | | |
| 9 | Glycerine | | | 234.75 | | |
| 10 | Fructose Corn | | | 234.75 | | |

TABLE 8-continued

Compositions to study effect of pH

| S. No. | Ingredients | Composition (mg/mL) | | | | |
|---|---|---|---|---|---|---|
| | | B1 | B2 | B3 | B4 | B5 |
| 11 | Syrup Citric Acid anhydrous | | | 0.15 | | |
| 12 | Sodium citrate dihydrate | | | 0.07 | | |
| 13 | Sucralose | | | 4.71 | | |
| 14 | 1N Hydrochloric acid | Q.S. | Q.S. | — | — | — |
| 15 | 1N Sodium hydroxide | — | — | Q.S. | Q.S. | Q.S. |
| | Final pH adjusted to | 3.5 | 4.0 | 4.5 | 5.0 | 5.5 |
| | Total | | | 1175.0 | | |

Manufacturing Procedure of Compositions B1 to B5:

Propylene glycol, Polysorbate 80 and purified water were mixed together in a suitable container. Sodium lauryl sulfate and povidone was added to above solution and mixed continuously at room temperature. Methyl paraben and propyl paraben were added and stirred continuously. The solution was heated under continuous stirring at 60° C.±2° C. and apixaban was added under continuous stirring until a clear solution is formed. Temperature of above solution was brought to room temperature under continuous stirring. Glycerin, sweetener and buffering agents were added under continuous stirring. Final pH was adjusted accordingly, using either 1N hydrochloric acid or 1N Sodium hydroxide solution. Final solution was filtered to get a clear solution.

TABLE 9

Initial and stability analysis data of Composition B1

| | Composition B1 | | | | |
|---|---|---|---|---|---|
| Parameters | Initial | 2 W 60° C. | 1 M 40° C./75% RH | 2 M | 1 M 25° C./60% RH |
| Description | Clear, colourless solution | Clear, colourless solution | Clear pale yellow (very low intensity) colour solution | Clear, colourless solution | |
| pH | 3.64 | 3.37 | 3.50 | 3.39 | 3.52 |
| Assay | 107.1 | 101.7 | 104.8 | 104.0 | 105.4 |
| Methyl paraben | 106.8 | 106.3 | 105.8 | 106.3 | 105.7 |
| Propyl paraben | 107.8 | 106.8 | 106.3 | 105.6 | 106.2 |
| Related Substance (% w/w) | | | | | |
| dehydro Imp. | ND | ND | ND | ND | ND |
| Amino acid Imp. | 0.03 | 0.28 | 0.09 | 0.12 | 0.06 |
| Acid Imp. | ND | 0.07 | 0.02 | 0.05 | ND |
| Chloro Imp. | 0.02 | 0.02 | 0.02 | ND | 0.02 |
| Methyl ester Imp. | 0.05 | 0.05 | 0.04 | 0.05 | 0.05 |
| Ester Imp. | ND | ND | ND | 0.01 | ND |
| Total | 0.19 | 0.75 | 0.52 | 0.95 | 0.34 |

TABLE 10

Initial and stability analysis data of Composition B2

| | Composition B2 | | | | |
|---|---|---|---|---|---|
| Parameters | Initial | 2 W 60° C. | 1 M 40° C./75% RH | 2 M | 1 M 25° C./60% RH |
| Description | Clear, colourless solution | Clear, slightly pale-yellow colour solution | Clear, colourless solution | Clear, colourless solution | Clear, colourless solution |
| pH | 4.06 | 3.86 | 4.07 | 3.86 | 4.05 |
| Assay | 107.5 | 104.2 | 105.3 | 105.5 | 105.8 |
| Methyl paraben | 107.1 | 106.5 | 105.9 | 105.9 | 106.1 |
| Propyl paraben | 107.9 | 107.2 | 106.3 | 106.0 | 106.5 |
| Related Substance (% w/w) | | | | | |
| dehydro Imp. | ND | ND | ND | ND | ND |
| Amino acid Imp. | ND | 0.15 | 0.03 | 0.03 | 0.02 |
| Acid Imp. | ND | 0.04 | ND | 0.01 | ND |
| Chloro Imp. | 0.02 | 0.02 | 0.02 | 0.02 | 0.02 |
| Methyl ester Imp. | 0.05 | 0.05 | 0.05 | 0.05 | 0.05 |
| Ester Imp. | ND | ND | ND | 0.01 | ND |
| Total | 0.17 | 0.59 | 0.34 | 0.57 | 0.24 |

TABLE 11

Initial and stability analysis data of Composition B3

| Parameters | Composition B3 | | | | |
|---|---|---|---|---|---|
| | Initial | 2 W 60° C. | 1 M 40° C./75% RH | 2 M | 1 M 25° C./ 60% RH |
| Description | Clear, colourless solution | Clear, slightly pale-yellow colour solution | Clear pale yellow (very low intensity) colour solution | Clear, colourless solution | |
| pH | 107.7 | 102.9 | 105.7 | 105.8 | 106.0 |
| Assay | 107.2 | 106.6 | 105.9 | 106.0 | 106.0 |
| Methyl paraben | 108.5 | 107.3 | 106.3 | 105.9 | 106.4 |
| Propyl paraben | 4.41 | 4.52 | 4.37 | 4.32 | 4.34 |

TABLE 11-continued

Initial and stability analysis data of Composition B3

| Parameters | Composition B3 | | | | |
|---|---|---|---|---|---|
| | Initial | 2 W 60° C. | 1 M 40° C./75% RH | 2 M | 1 M 25° C./ 60% RH |
| Related Substance (% w/w) | | | | | |
| dehydro Imp. | ND | ND | ND | ND | ND |
| Amino acid Imp. | ND | 0.08 | 0.02 | 0.01 | ND |
| Acid Imp. | ND | ND | 0.01 | 0.01 | ND |
| Chloro Imp. | 0.03 | 0.01 | 0.02 | 0.02 | 0.02 |
| Methyl ester Imp. | 0.05 | 0.05 | 0.05 | 0.06 | 0.05 |
| Ester Imp. | ND | ND | ND | 0.01 | ND |
| Total | 0.18 | 0.42 | 0.28 | 0.41 | 0.24 |

TABLE 12

Initial and stability analysis data of Composition B4

| Parameters | Composition B4 | | | | |
|---|---|---|---|---|---|
| | Initial | 2 W 60° C. | 1 M 40° C./75% RH | 2 M | 1 M 25° C./ 60% RH |
| Description | Clear, colourless solution | Clear, slightly pale-yellow colour solution | Clear, colourless solution | Clear, colourless solution | Clear, colourless solution |
| pH | 106.7 | 104.1 | 105.5 | 105.8 | 105.8 |
| Assay | 106.4 | 106.2 | 105.9 | 105.5 | 105.8 |
| Methyl paraben | 107.3 | 106.4 | 106.3 | 106.0 | 106.2 |
| Propyl paraben | 4.96 | 4.50 | 4.90 | 4.78 | 4.93 |
| Related Substance (% w/w) | | | | | |
| dehydro Imp. | ND | ND | ND | ND | ND |
| Amino acid Imp. | ND | 0.05 | ND | ND | ND |
| Acid Imp. | ND | ND | ND | ND | ND |
| Chloro Imp. | 0.02 | 0.02 | 0.01 | 0.03 | 0.03 |
| Methyl ester Imp. | 0.05 | 0.05 | 0.05 | 0.08 | 0.05 |
| Ester Imp. | ND | ND | ND | 0.01 | ND |
| Total | 0.12 | 0.38 | 0.19 | 0.43 | 0.23 |

TABLE 13

Initial and stability analysis data of Composition B5

| Parameters | Composition B5 | | | | |
|---|---|---|---|---|---|
| | Initial | 2 W 60° C. | 1 M 40° C./75% RH | 2 M | 1 M 25° C./ 60% RH |
| Description | Clear, colourless solution | Clear, slightly pale-yellow colour solution | Clear, colourless solution | Clear pale yellow (very low intensity) colour solution | Clear, colourless solution |
| pH | 107.0 | 104.3 | 105.6 | 105.9 | 105.7 |
| Assay | 106.7 | 106.2 | 105.8 | 105.7 | 105.8 |
| Methyl paraben | 107.9 | 106.5 | 106.2 | 105.7 | 106.2 |
| Propyl paraben | 5.45 | 4.77 | 5.16 | 5.03 | 5.34 |
| Related Substance (% w/w) | | | | | |
| dehydro Imp. | ND | ND | ND | ND | ND |
| Amino acid Imp. | ND | ND | ND | ND | ND |
| Acid Imp. | ND | ND | ND | ND | ND |

TABLE 13-continued

Initial and stability analysis data of Composition B5

| Parameters | Composition B5 | | | | |
|---|---|---|---|---|---|
| | Initial | 2 W 60° C. | 1 M 40° C./75% RH | 2 M | 1 M 25° C./ 60% RH |
| Chloro Imp. | 0.03 | 0.03 | 0.02 | 0.02 | 0.03 |
| Methyl ester Imp. | 0.05 | 0.05 | 0.05 | 0.05 | 0.05 |
| Ester Imp. | ND | ND | ND | 0.01 | ND |
| Total | 0.17 | 0.33 | 0.22 | 0.28 | 0.22 |

Observation: The Compositions B1 to B5 having pH between 3.5 to 5.5 were both physically and chemically stable for at least 2 months at 40° C./75% RH condition, without visible particles and with no significant change in assay and impurity profile.

Example 3

Apixaban compositions were set forth in Table 14

TABLE 14

Compositions to study effect of different concentrations of povidone

| S. No. | Ingredients | Composition (mg/mL) | | |
|---|---|---|---|---|
| | | C1 | C2 | C3 |
| 1 | Apixaban | 0.400 | 0.400 | 0.400 |
| 2 | Propylene Glycol | 384.52 | 354.52 | 402.02 |
| 3 | Polysorbate 80 | 8.30 | 8.30 | 8.30 |
| 4 | Povidone (K 25) | 30.00 (2.5%) | 60.00 (5%) | 12.50 (1.0%) |
| 5 | Sodium lauryl sulphate | 12.00 | 12.00 | 12.00 |
| 6 | Methyl paraben | 1.763 | 1.763 | 1.763 |
| 7 | Propyl Paraben | 0.176 | 0.176 | 0.176 |
| 8 | Glycerine | 234.75 | 234.75 | 234.75 |
| 9 | Fructose Corn Syrup | 234.75 | 234.75 | 234.75 |
| 10 | Citric Acid anhydrous | 0.15 | 0.15 | 0.15 |
| 11 | Sodium citrate dihydrate | 0.07 | 0.07 | 0.07 |
| 12 | Sucralose | 4.71 | 4.71 | 4.71 |
| 13 | Orange flavor | — | — | 3.00 |
| 14 | Purified water | 263.41 | 263.41 | 260.41 |
| | Total | 1177.0 | 1175.0 | 1175.0 |

Manufacturing Procedure of Compositions C1 to C3:

Propylene glycol, Polysorbate 80 and purified water were mixed together in a suitable container. Sodium lauryl sulfate and povidone was added to above solution and mixed continuously at room temperature. Methyl paraben and propyl paraben were added and stirred continuously. The solution was heated under continuous stirring at 40° C.±5° C. and apixaban was added under continuous stirring until a clear solution is formed. Temperature of above solution was brought to room temperature under continuous stirring. Glycerine, sweetener and buffering agents were added under continuous stirring. Final solution was filtered to get a clear solution.

TABLE 15

Initial and Stability analysis data of Composition C1

| Parameter | Composition C1 | | | |
|---|---|---|---|---|
| | Initial | 2 W 60° C. | 1 M 40° C./ 75% RH | 1 M 25° C./ 60% RH |
| Description | Clear, colourless solution | | | |
| Assay | 109.1 | 98.4 | 99.1 | 99.4 |
| Methyl paraben | 108.8 | 98 | 98.5 | 98.3 |
| Propyl paraben | 113 | 101.9 | 102.2 | 101.9 |
| pH | 4.13 | 4.15 | 4.18 | 4.19 |
| Related Substance (% w/w) | | | | |
| dehydro Imp. | ND | ND | ND | ND |
| Amino acid Imp. | ND | ND | 0.03 | 0.02 |
| Acid Imp. | ND | ND | ND | ND |
| Chloro Imp. | 0.03 | 0.02 | 0.02 | 0.01 |
| Methyl ester Imp. | 0.05 | 0.05 | 0.05 | 0.05 |
| Ester Imp. | ND | ND | ND | ND |
| Total Impurities | 0.17 | 0.18 | 0.26 | 0.20 |

Observation: The Composition C1 was physically and chemically stable for at least 1 month at 60° C., 40° C./75% RH and 25° C./60% RH condition, without visible particles and with no significant change in assay and impurity profile.

Example 4

Apixaban compositions were prepared, as set forth in Table 16.

TABLE 16

Apixaban Composition D

| Sr. No. | Ingredients | Composition D | |
|---|---|---|---|
| | | mg/mL | % w/w |
| 1 | Apixaban | 0.400 | 0.037 |
| 2 | Propylene Glycol | 365.000 | 33.486 |
| 3 | Polysorbate 80 | 8.300 | 0.761 |
| 4 | Sodium lauryl sulphate | 12.000 | 1.101 |
| 5 | Methyl paraben | 1.763 | 0.162 |
| 6 | Propyl Paraben | 0.176 | 0.016 |
| 7 | Glycerine | 235.000 | 21.560 |
| 8 | Citric Acid anhydrous | 0.150 | 0.014 |
| 9 | Sodium citrate dihydrate | 0.350 | 0.032 |
| 10 | Sucralose | 2.000 | 0.183 |
| 11 | Povidone | 47.000 | 4.312 |
| 12 | Orange flavor | 3.000 | 0.275 |
| 13 | 2.7N Hydrochloric acid | Q.S. to adjust pH | — |
| 14 | 1N Sodium hydroxide | | |
| 15 | Purified water | 414.860 | 38.061 |

The Composition D was physically and chemically stable for at least 6 months at 40° C./75% RH and 25° C./60% RH condition, without visible particles and with no significant change in assay and impurity profile.

TABLE 17

Apixaban Composition D Testing Data

| | | Composition D | |
|---|---|---|---|
| Parameter | Initial | 6 M 25° C./ 60% RH | 6 M 40° C./ 75% RH |
| Description | Clear colorless to yellow solution, free from visible particles | | |
| Assay | 100.5 | 101.1 | 100.6 |
| pH | 5.0 | 5.1 | 5.2 |
| Related Substance (% w/w) | | | |
| Acid Imp. | ND | ND | ND |
| Amino acid Imp. | ND | ND | ND |
| Dehydro Imp. | ND | 0.06 | 0.07 |
| Total Impurities | NA | 0.12 | 0.20 |

Figure 1:
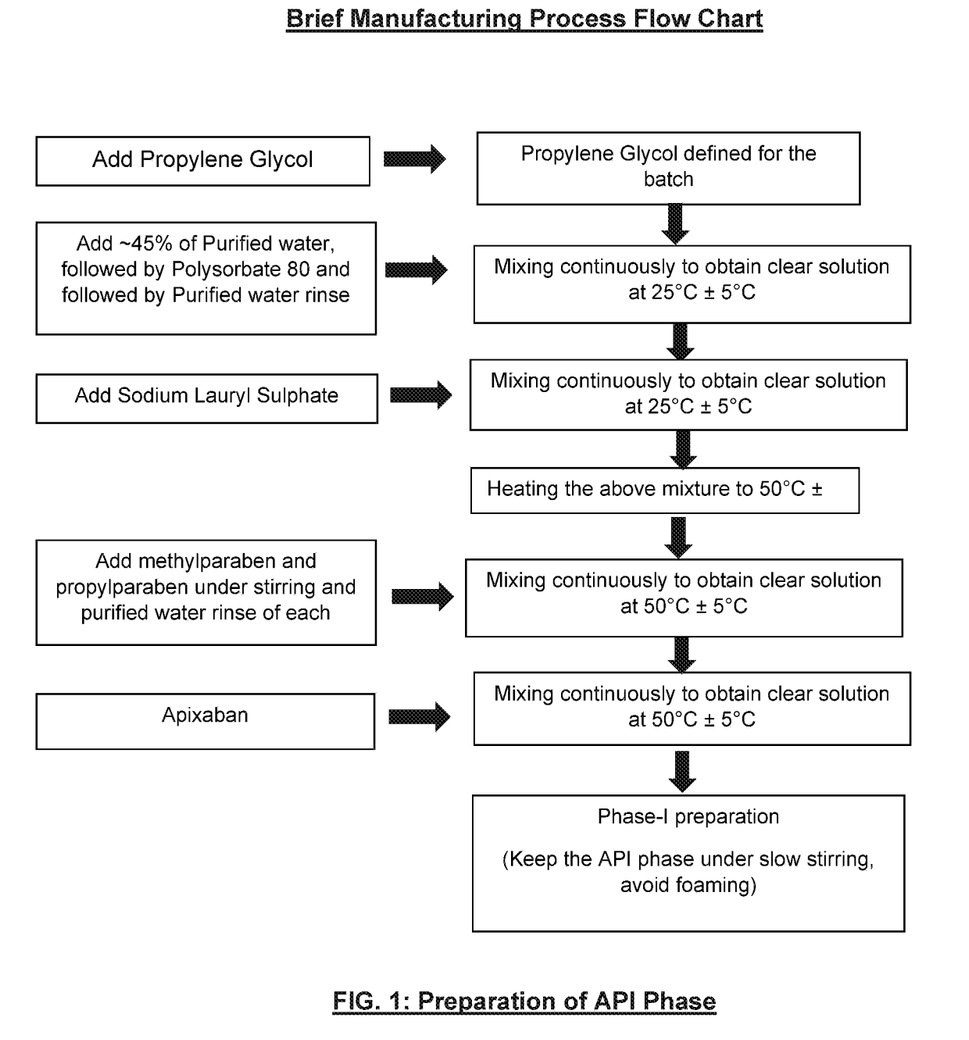
FIG. 1: Preparation of API phase
Figure 2:
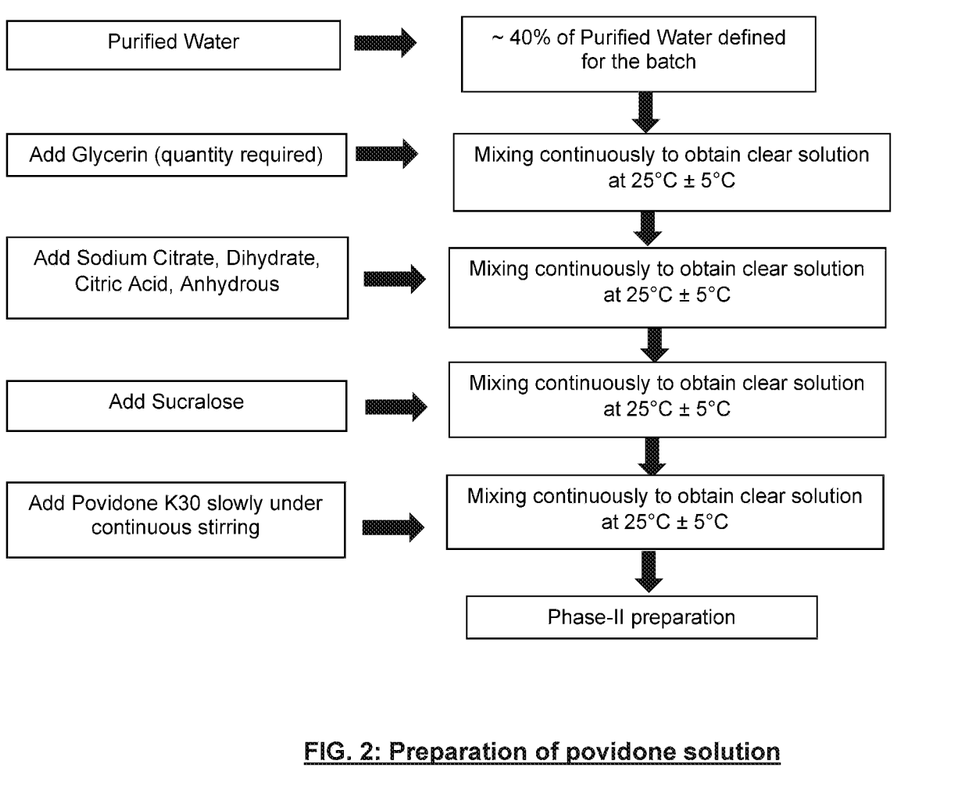
FIG. 2: Preparation of povidone solution
Figure 3:
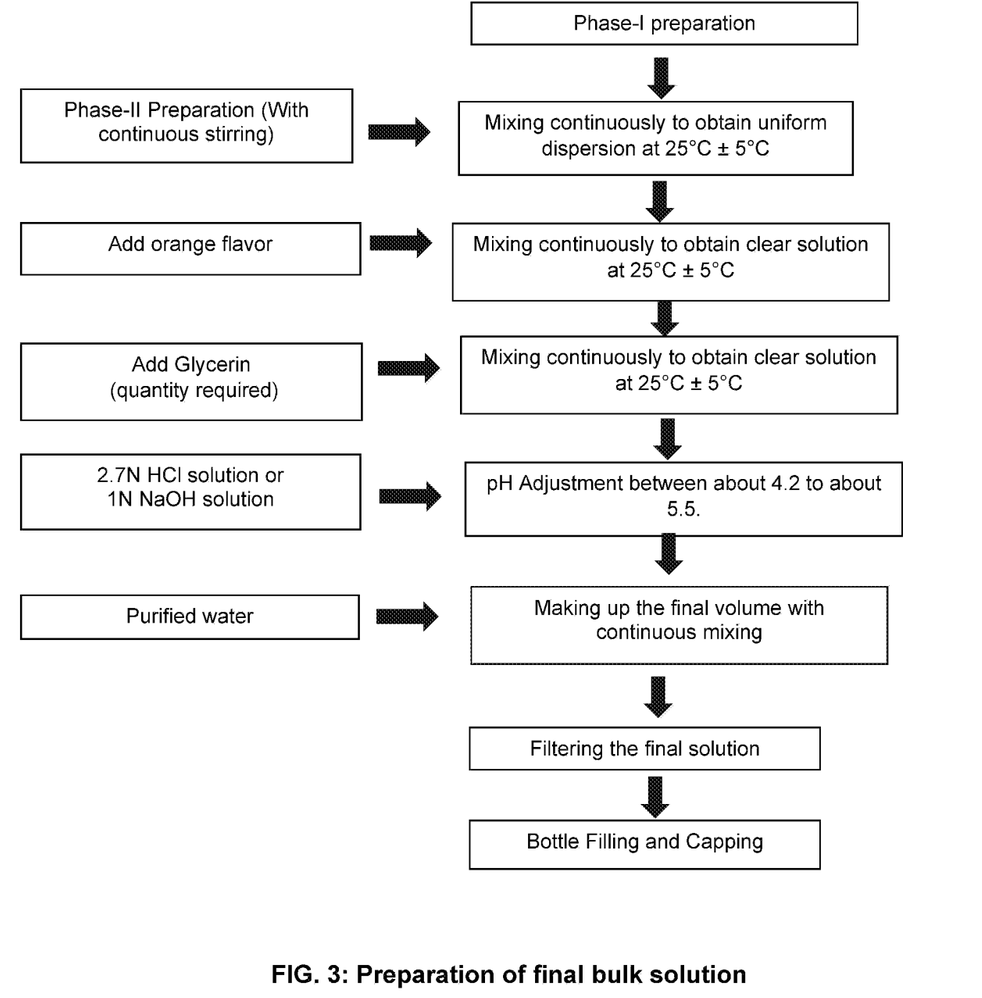
FIG. 3: Preparation of final bulk solution

Brief manufacturing process flow charts are as described in FIGS. 1, 2 and 3.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

What is claimed is:

1. A stable oral solution comprising of:
   (i) apixaban at a concentration of about 0.4 mg/mL;
   (ii) water at a concentration of about 38% w/w;
   (iii) polysorbate at a concentration of about 0.7% w/w,
   (iv) propylene glycol at a concentration of about 33% w/w;
   (v) sodium lauryl sulphate at a concentration of about 1% w/w;
   (vi) glycerin at a concentration of about 21% w/w,
   (viii) polyvinyl pyrrolidone at a concentration of about 4% w/w,
   (ix) a preservative at a concentration of about 0.1% w/w,
   (x) a buffering agent at a concentration about 0.04% w/w,
   (xi) a pH adjusting agent at a concentration of 0% w/w to about 5% w/w,
   (xii) a sweetener at a concentration of about 0.2% w/w, and
   (xiii) a flavoring agent at a concentration of about 0.3% w/w;
   wherein the stable oral solution is free of polyethylene glycol;
   wherein the oral solution is physically stable for at least 6 months at 40° C./75% RH and at 25° C./60% RH,
   wherein the oral solution is chemically stable with no more than 10% loss of apixaban for at least 6 months at 40° C./75% RH and at 25° C./60% RH,
   wherein the buffering agent is citric acid and sodium citrate dihydrate; and
   wherein the pH adjusting agent is HCl, NaOH or a combination thereof.

2. The stable oral solution according to claim 1, wherein a level of the 1-(4-methoxyphenyl)-7-oxo- 6-(4-(2-oxopiperidin-1-yl)phenyl)-4,5,6,7-tetrahydro-1H-pyrazolo [3,4-c] pyridine-3-carboxylic acid impurity is less than about 0.5% w/w as determined by HPLC at a wavelength of 270 nm.

3. The stable oral solution according to claim 1, wherein a level of the 5- ((4-(3-carbamoyl-1-(4-methoxy phenyl)-7oxo-1,4,5,7-tetrahydro-6H-pyrazolo[3,4c]pyridin-6-yl)phenyl)amino) pentanoic acid impurity is less than about 0.5% w/w as determined by HPLC at a wavelength of 270 nm.

4. The stable oral solution according to claim 1, wherein a level of the 1- (4-methoxyphenyl)-7-oxo-6-(4-(2-oxopiperidin-1-yl)phenyl)-6,7-dihydro-1H-pyrazolo[3,4- c]pyridine-3-carboxamide impurity is less than about 0.5% w/w as determined by HPLC at a wavelength of 270 nm.

5. A stable oral solution comprising:
   (i) apixaban at a concentration of about 0.4 mg/mL;
   (ii) water at a concentration of about 38% w/w;
   (iii) polysorbate at a concentration of about 0.7% w/w,
   (iv) propylene glycol at a concentration of about 33% w/w;
   (v) sodium lauryl sulphate at a concentration of about 1% w/w;
   (vi) glycerin at a concentration of about 21% w/w,
   (viii) polyvinyl pyrrolidone at a concentration of about 4% w/w,
   (ix) a preservative at a concentration of about 0.1% w/w,
   (x) a buffering agent at a concentration about 0.04% w/w,
   (xi) a pH adjusting agent at a concentration of 0% w/w to about 5% w/w,
   (xii) a sweetener at a concentration of about 0.2% w/w, and
   (xiii) a flavoring agent at a concentration of about 0.3% w/w;
   wherein the stable oral solution is free of polyethylene glycol;
   wherein the oral solution is physically stable for at least 6 months at 40° C./75% RH and at 25° C./60% RH,
   wherein the oral solution is chemically stable with no more than 10% loss of apixaban for at least 6 months at 40° C./75% RH and at 25° C./60% RH,
   wherein the buffering agent is citric acid and sodium citrate dihydrate; and
   wherein the pH adjusting agent is HCl, NaOH or a combination thereof.

6. The stable oral solution comprising:
   (i) apixaban at a concentration of about 0.4 mg/mL;
   (ii) water at a concentration of about 260 to about 270 mg/mL;
   (iii) polysorbate at a concentration of about 5-10 mg/mL;
   (iv) propylene glycol at a concentration of about 350-440 mg/mL;
   (v) sodium lauryl sulphate at a concentration of about 10-15 mg/mL;
   (vi) glycerin at a concentration of about 230-240 mg/mL;
   (viii) polyvinyl pyrrolidone at a concentration of about 12-60 mg/mL or hydroxypropyl methyl cellulose at a concentration of about 10 mg/mL;
   (ix) a preservative at a concentration of about 1-3 mg/mL;
   (x) a buffering agent at a concentration about 0.2-1.0 mg/mL;
   (xi) a pH adjusting agent at a concentration of 0% w/w to about 5% w/w,
   (xii) a sweetener at a concentration of about 2-240 mg/mL; and
   (xiii) a flavoring agent at a concentration of about 0-5 mg/mL;
   wherein the stable oral solution is free of polyethylene glycol;

wherein the pH of the stable oral solution is about 3 to about 8;

wherein the oral solution is physically stable for at least 6 months at 40° C./75% RH and at 25° C./60% RH, wherein the oral solution is chemically stable with no more than 10% loss of apixaban for at least 6 months at 40° C./75% RH and at 25° C./60% RH, wherein the buffering agent is citric acid and sodium citrate dihydrate; and wherein the pH adjusting agent is HCl, NaOH or a combination thereof.

7. The stable oral solution according to claim 6, wherein the stable oral solution consists of components (i)-(xiii).

8. The stable oral solution according to claim 6, wherein the pH of the stable oral solution is about 4 to about 6.

9. The stable oral solution according to claim 6, wherein the pH of the stable oral solution is about 4.5 to about 5.5.

10. The stable oral solution according to claim 6, wherein at least one of the following conditions are met;
    (a) the preservative is methyl paraben, propyl paraben, or a combination thereof;
    (b) the sweetener is fructose corn syrup, sucralose, or a combination thereof; or
    (c) the flavoring agent is orange flavor.

11. The stable oral solution according to claim 6, wherein the stable oral solution comprises:
    (ii) water at a concentration of about 260-265 mg/mL;
    (iii) polysorbate at a concentration of about 5-10 mg/mL;
    (iv) propylene glycol at a concentration of about 360-370 mg/mL;
    (v) sodium lauryl sulphate at a concentration of about 10-15 mg/mL;
    (vi) glycerin at a concentration of about 230-235 mg/mL;
    (viii) polyvinyl pyrrolidone at a concentration of about 45-50 mg/mL;
    (ix) a preservative at a concentration of about 1 mg/mL;
    (x) a buffering agent at a concentration about 0.2-0.5 mg/mL;
    (xii) a sweetener at a concentration of about 235-240 mg/mL; and
    (xiii) a flavoring agent at a concentration of about 2-3 mg/mL.

12. The stable oral solution according to claim 6, wherein the stable oral solution comprises:
    (ii) water at a concentration of about 460-465 mg/mL;
    (iii) polysorbate at a concentration of about 5-10 mg/mL;
    (iv) propylene glycol at a concentration of about 430-440 mg/mL;
    (v) sodium lauryl sulphate at a concentration of about 10-15 mg/mL;
    (vi) glycerin at a concentration of about 235 mg/mL;
    (viii) hydroxypropyl methyl cellulose at a concentration of about 10 mg/mL;
    (ix) a preservative at a concentration of about 2-3 mg/mL;
    (x) a buffering agent at a concentration about 0.2-0.5 mg/mL; and
    (xii) a sweetener at a concentration of about 4-5 mg/mL.

13. The stable oral solution according to claim 6, wherein the stable oral solution comprises:
    (ii) water at a concentration of about 260-265 mg/mL;
    (iii) polysorbate at a concentration of about 5-10 mg/mL;
    (iv) propylene glycol at a concentration of about 360-370 mg/mL;
    (v) sodium lauryl sulphate at a concentration of about 10-15 mg/mL;
    (vi) glycerin at a concentration of about 230-235 mg/mL;
    (viii) polyvinyl pyrrolidone at a concentration of about 45-50 mg/mL;
    (ix) a preservative at a concentration of about 2-3 mg/mL;
    (x) a buffering agent at a concentration about 0.2-0.5 mg/mL; and
    (xii) a sweetener at a concentration of about 235-240 mg/mL.

14. The stable oral solution according to claim 6, wherein the stable oral solution comprises:
    (ii) water at a concentration of about 260-265 mg/mL;
    (iii) polysorbate at a concentration of about 5-10 mg/mL;
    (iv) propylene glycol at a concentration of about 380-385 mg/mL;
    (v) sodium lauryl sulphate at a concentration of about 10-15 mg/mL;
    (vi) glycerin at a concentration of about 230-235 mg/mL;
    (viii) polyvinyl pyrrolidone at a concentration of about 30 mg/mL;
    (ix) a preservative at a concentration of about 1-2 mg/mL;
    (x) a buffering agent at a concentration about 0.2-0.5 mg/mL; and
    (xii) a sweetener at a concentration of about 235-240 mg/mL.

15. The stable oral solution according to claim 6, wherein the stable oral solution comprises:
    (ii) water at a concentration of about 260-265 mg/mL;
    (iii) polysorbate at a concentration of about 5-10 mg/mL;
    (iv) propylene glycol at a concentration of about 350-360 mg/mL;
    (v) sodium lauryl sulphate at a concentration of about 10-15 mg/mL;
    (vi) glycerin at a concentration of about 230-235 mg/mL;
    (viii) polyvinyl pyrrolidone at a concentration of about 60 mg/mL;
    (ix) a preservative at a concentration of about 1-2 mg/mL;
    (x) a buffering agent at a concentration about 0.2-0.5 mg/mL; and
    (xii) a sweetener at a concentration of about 235-240 mg/mL.

16. The stable oral solution according to claim 6, wherein the stable oral solution comprises:
    (ii) water at a concentration of about 260-265 mg/mL;
    (iii) polysorbate at a concentration of about 5-10 mg/mL;
    (iv) propylene glycol at a concentration of about 400-405 mg/mL;
    (v) sodium lauryl sulphate at a concentration of about 10-15 mg/mL;
    (vi) glycerin at a concentration of about 230-235 mg/mL;
    (viii) polyvinyl pyrrolidone at a concentration of about 10-15 mg/mL;
    (ix) a preservative at a concentration of about 1-2 mg/mL;
    (x) a buffering agent at a concentration about 0.2 mg/mL;
    (xii) a sweetener at a concentration of about 235-240 mg/mL; and
    (xiii) a flavoring agent at a concentration of about 2-4 mg/mL.

* * * * *